United States Patent [19]

Dineen et al.

[11] 4,351,063

[45] Sep. 21, 1982

[54] X-RAY DIFFRACTION APPARATUS

[75] Inventors: Colin Dineen, Buckinghamshire; Christopher A. Wallace, London, both of England

[73] Assignee: Elliott Brothers (London) Limited, Chelmsford, England

[21] Appl. No.: 181,851

[22] Filed: Aug. 27, 1980

[30] Foreign Application Priority Data

Aug. 28, 1979 [GB] United Kingdom ............... 7929729

[51] Int. Cl.³ .......................................... G01M 23/20
[52] U.S. Cl. ...................................... 378/79; 378/84
[58] Field of Search ...................... 250/280, 272, 273

[56] References Cited
U.S. PATENT DOCUMENTS 2,853,617 9/1958 Berreman ............................ 250/280
4,078,175 3/1978 Fletcher ............................... 250/280

Primary Examiner—Craig E. Church

Attorney, Agent, or Firm—Kirschstein, Kirschstein, Ottinger & Cobrin

[57] ABSTRACT

Semiconductor crystals for use, for example, in the manufacture of integrated circuits are required to be inspected for crystal lattice perfection before any subsequent circuit processing. This can be done by X-ray diffraction in which the crystal is curved so that a divergent beam irradiates all points of the crystal surface at the same angle and simultaneously. The difficulty is however, in holding the crystal in the appropriately curved form while at the same time not obstructing the passage of X-rays from the front or back of the crystal and so enable topographs to be obtained by both reflection and transmission. According to the invention, in such a system the crystal is attached to a flat, X-ray transparent plate by pneumatic X-ray transparent means, and the plate is deformed to the required curvature, carrying the crystal with it.

3 Claims, 5 Drawing Figures

X-RAY DIFFRACTION APPARATUS

This invention relates to X-ray diffraction apparatus and particularly to such apparatus employed for the inspection of crystals in the form of plates or slices.

An important but not exclusive application of the invention is to the inspection of crystals for use in the manufacture of integrated circuits. In such manufacture the basic component is a block of semiconductor material, e.g. silicon, in which the various circuit components are formed. It is clearly important therefore, that the crystal structure is perfect, without any faults, ruptures or foreign bodies. It is known that crystal structure can be investigated by irradiating the crystal with X-rays of a particular wavelength and examining the diffraction topograph that results from reflection or transmission of the X-rays from or through the crystal. Faults in the crystal structure are readily apparent in irregularities in the diffraction topograph. It is very desirable, if not essential, for a full assessment of a crystal, that topographs produced by both reflection and transmission are available to provide information from different levels within the crystal.

A known method of producing the diffraction topograph is to collimate the X-ray beam to a line cross-section and, in effect, to sweep it broadside across the crystal specimen keeping a reference plane of the crystal at a constant angle to the beam axis to achieve the desired diffraction of the X-ray beam. In fact it is much more convenient to move the crystal and this is what is done in this method. X-ray plates on which the diffracted rays are projected and recorded require a long exposure if high resolution is to be obtained. The time taken, therefore, to scan the crystal is, by this known method, inordinately long.

It has been proposed that this difficulty could be overcome, in the case of a crystal in the form of a slice of material, by curving the crystal slice in such a way that the angle of incidence of a divergent beam from a predetermined source to any point on the crystal is constant. The necessary curve to achieve this, at least in a central plane through, and normal to, the crystal is a logarithmic spiral centred on the X-ray source. A suitably divergent beam can then irradiate the whole crystal simultaneously and the overall exposure time is greatly reduced. Arrangements of this kind are shown in FIGS. 1 and 2 of the accompanying drawings, FIG. 1 showing a transmission method and FIG. 2 a reflection method.

In FIG. 1 the crystal 1 lies on a logarithmic spiral 2 at the centre of which is an X-ray source 3. An X-ray plate 4 receives diffracted radiation 5 by transmission through the crystal. In the alternative method of FIG. 2, the source 3 again lies at the centre of a logarthmic spiral 2 and the X-ray plate 4 is positioned to receive diffracted radiation 5 which is, in effect, reflected from the crystal 1. The spirals and incident angles are different in the two cases. Topographs produced by both methods are necessary to provide a complete picture of the crystal structure and it is a feature of the present invention that the apparatus can employ the transmission method just as easily as it can the reflection method.

In practice, the curving of the crystal slice, which may be circular or rectangular, is difficult to achieve if the requirements are to be met that the crystal surface must be absolutely unmarked and undamaged in any way in the process, and in addition any mounting plate or attachment device must, at least in the case of the transmission arrangement, cause as little attenuation as possible and cast no X-ray shadows.

It is an object of the present invention therefore to provide X-ray diffraction apparatus in which a crystal slice can be mounted and held in a curved form while meeting these requirements.

According to the present invention, in X-ray diffraction apparatus which includes a mounting plate for a crystal slice which is to be inspected, and means for imposing a curvature on the mounting plate and thereby on a crystal mounted on it, the curvature of the mounting plate being such that the whole crystal or a significant part of it can be irradiated at a constant incident angle by a suitably positioned X-ray source so as to produce, by transmission through or reflection from the crystal, a diffraction topograph indicative of the crystal structural perfection, pneumatic pressure clamping means is provided for clamping the crystal to the mounting plate, the mounting plate and the clamping means being transparent to X-rays to permit both transmission and reflection topographs to be obtained.

A layer of elastic material transparent to X-rays covering the mounting plate may be used to cushion the crystal slice against localised distortion that may arise from the presence of hard dust particles between the mounting plate and the crystal slice.

The clamping means preferably includes a sheet of flexible material transparent to X-rays arranged to overlie the crystal and mounting plate so that a peripheral chamber is formed in operation between the edge of the crystal and the sheet of material, which chamber can be evacuated through a hole in the mounting plate. This sheet of material preferably has a hole arranged to expose the central part of the crystal.

The clamping means may, alternatively, comprise an inflatable annulus of flexible sheet material transparent to X-rays, containing gas, and of such extent as to overlie the edge of a crystal slice, further clamping means being arranged to engage the mounting plate and bear upon the annulus so as to compress the gas within it and clamp the crystal slice pneumatically against the mounting plate. The further clamping means may be mechanical or may comprise a sheet of flexible material transparent to X-rays and covering the annulus at least in part so as to form an annular chamber between the inflatable annulus, the sheet of flexible material, and the mounting plate, means being provided for evacuating the annular chamber.

The cross-section of the mounting plate in the region of the crystal may be adapted to accommodate the stiffness of a crystal while maintaining the required curvature of the crystal.

According to another aspect of the invention, in a method of mounting a crystal slice on a crylindrical surface for irradiation from a source of X-rays, the crystal slice is held against the appropriately curved surface of a transparent mounting plate by pneumatic sealing means transparent to X-rays.

One embodiment of X-ray diffraction apparatus according to the invention, will now be described, by way of example, with reference to the accompanying drawings, of which:

Figure 1:
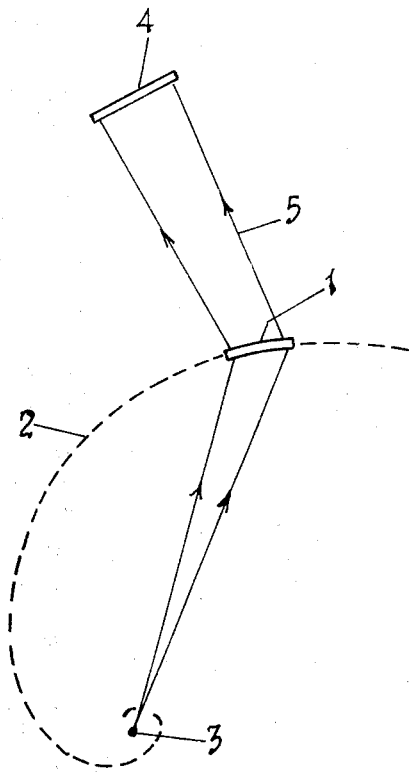
FIGS. 1 and 2 are diagrams of a crystal slice curved to permit overall irradiation at a constant incident angle and arranged for transmission and reflection respectively.

Referring to the drawings, FIG. 1 shows, as mentioned above, a known arrangement for avoiding the scanning of the crystal 1 by the source 3. The crystal 1 is made to conform to a cylindrical surface 2 of logarithmic spiral form so that at all points on the crystal surface the diverging beam from the X-ray source 3 is incident at the same angle. The diffracted beam 5 diverges on transmission to an X-ray sensitive plate 4 to produce the diffraction topograph. In the alternative arrangement of FIG. 2 a diffracted beam 5' arising from reflection of the beam from the crystal rather than transmission through it, converges away from the crystal to an X-ray plate 4'.

With cylindrical curvature of the crystal, the incident angle does of course, vary from the required constant value at points on the crystal out of the plane of the logarithmic spiral (i.e. the plane of FIG. 1). However, the change of angle from this cause is small and the finite size of a practicable X-ray source is such that an alternative point on the source can produce the same incident beam angle at points out of the plane of the figure.

Figure 2:
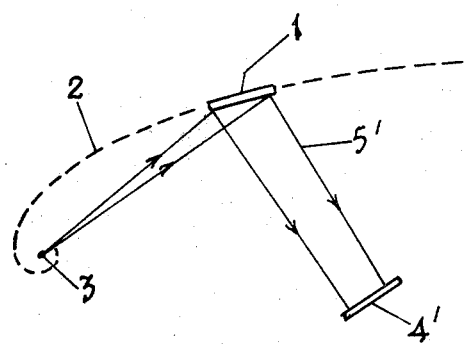

FIG. 2 shows the manner in which a cylindrical logarithmic curve is obtained. A mounting plate 6 of X-ray transparent material and of rectangular form (the edge of which is shown) is held between rods 7 at one end and 8 at the other. The rods 7 and 8 are movable transverse to the plate 6 so as to be able to compress the plate 6 between them. Each pair of rods is out of alignment so that a bending moment is imposed on the plate 6 of magnitude depending upon the force applied and the distance between the paths of the rods. The bending moments are of opposite hand so that the plate 6 is deformed into a concave/convex form. The two bending moments can be adjusted relatively by adjustment of the rod spacings $d_1$ and $d_2$. As shown, the spacing $d_1$ is greater than that of $d_2$, so that, with the same applied forces on the rods the curvature will be greater at the rod 7 end. In this manner a curvature can be obtained which is a close approximation to a section of a logarithmic spiral. All of the crystal lattice planes can thereby be held at the same angle to the incident radiation from a point source at the centre of the spiral.

In an alternative method of achieving the same curvature, the spacings $d_1$ and $d_2$ are made equal and the applied forces are made different. Clearly any combination of spacing and force adjustment may be used to achieve the same effect.

In either arrangement however, it is important that the X-ray obstructing rods 7 and 8, and any structure which supports them, do not obstruct any of the X-ray paths, in reflection or transmission.

Figure 3:
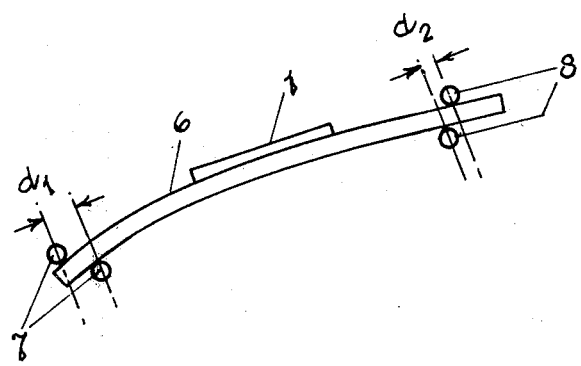
FIG. 3 is a diagrammatic side view of a mounting plate and attached crystal slice showing means for imposing the required curvature on the mounting plate.

The crystal 1 is shown simply attached to the mounting plate 6 in FIG. 3 but this attachment is in fact one of the major difficulties of the whole process. First of all the ideal curvature of the crystal must be maintained as closely as possible and the crystal must therefore be clamped quite firmly to the mounting plate. The crystal face (at least the active face which is to be subsequently processed for the purposes of the integrated circuit) must be untouched by anything that would mark or damage it and preferably by anything at all. In addition no member or device must be used to attach it to the plate which would cast an X-ray shadow or which would attenuate the radiation excessively.

Certain of these requirements are in conflict, at least in the case of the transmission arrangement shown in FIGS. 1 and 3. In this case clearly the mounting plate must be transparent to X-rays and as thin as possible to reduce the attenuation. The thinner is the mounting plate however, the greater is the effect of the stiffness of the crystal itself and consequently there is a tendency for the curvature to depart from the ideal logarithmic spiral.

Figure 4A:
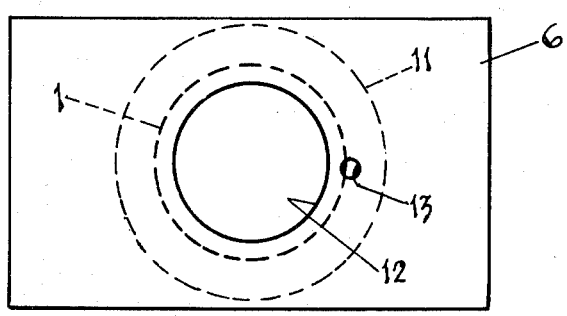
FIGS. 4(a) and (b) are plan and side views of a crystal slice mounted on a mounting plate in accordance with the invention.
Figure 4B:
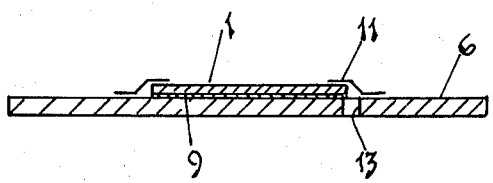

One embodiment of means for clamping the crystal slice 1 to the mounting plate 6 is shown diagrammatically in FIG. 4. The mounting plate 6 is a rectangular piece of perspex suitably 3 mm. thick. The crystal may range from $10\mu$ to 1 mm. thick and have a diameter up to 150 mm. but typically 50–100 mm. The plate 6 is substantially wider than the crystal so that edge effects on the plate do not affect the crystal.

The crystal 1 is laid on the plate 6 but spaced from it by a thin layer of highly elastic material 9 e.g. natural rubber. This intervening layer has the effect of enveloping any hard dust particles that there may be between the crystal and mounting plate and cushioning the crystal against any local distortion that it might otherwise endure. Damage due to such dust particles are thus, in general, completely avoided.

A sheet of material 11, which may be soft PVC, is then laid over the crystal. The sheet or film of soft plastic material extends over the edge of the crystal and rubber sheet 9, and down onto the plate 6 to form an annular chamber enclosed by the edge of the crystal, the plate 6 and the film 11. This annular chamber may then be evacuated by way of the hole 13 or by way of a channel (not shown) formed in the underside of the sheet 11, for example, by sticking strips of the same plastic sheeting on to it with a gap between the strips. When the sheet 11 is in contact with the crystal and plate 6 this channel forms an evacuation duct extending from the region of the annular chamber to a hole (not shown) in the plate by providing a connection between the channel and a vacuum source.

In a further alternative, a channel may be formed in the plate 6 between the annular chamber and a vacuum source. The film 11, being very thin and flexible (suitably thinner than $25\mu$), seals the chamber under atmospheric pressure, the crystal being pressed firmly to the plate 6 all around its edge by atmospheric pressure, since any space between the crystal and the plate has been evacuated. If the diffraction process is performed in any other gaseous medium the pressure is then the ambient pressure employed.

The central part of the crystal does not need to be covered with the film to ensure the seal and since it is preferable that this surface is touched by absolutely nothing solid, a hole 12 may be provided in the film 11 to leave an overlap of 1–2 mm. of the film 11 around the crystal edge. Although desirable, this hole 12 is not essential, since the film is non-crystalline and transparent to X-rays. Any dust particles that might possibly be trapped by the film will be embedded in it without damaging the crystal surface.

This method of curving the crystal has the advantage that the deforming forces are applied in an absolutely uniform manner by pneumatic pressure, i.e. mechanical forces are applied to the plate and not the crystal. In addition, removal of the crystal after the diffraction inspection is achieved very simply by 'letting down' the vacuum.

Clearly, a rectangular or other shaped crystal can be curved by this method just as easily as a circular one.

In some cases such as described, the crystal stiffness may not be negligible in comparison with the plate stiffness. In this case the crystal will distort the curvature of the plate and the crystal curvature will deviate from the ideal form. One solution to this problem is to recess the plate slightly to receive the crystal, the combined stiffness of the crystal and plate (when adhering by atmospheric pressure) being then such that the crystal/plate combination does not give excessive local stiffness.

In general, the cross-section of the plate can be engineered in a number of ways to keep the crystal curvature correct when the mounting plate is generally rather thin. The plate can be of composite layer construction, with layers of different material, the cross-section then differing in the crystal region and outside it.

The crystal may be mounted on the concave side of the mounting plate for both reflection and transmission but will normally be mounted on the convex side for transmission topographs only. In the case of a semiconductor integrated circuit it is important that the active face of the crystal is kept out of contact with anything solid and this face will therefore be outwards no matter which face of the plate the crystal is mounted on.

In an alternative embodiment to that of FIG. 4, the crystal slice is held on to the mounting plate by an inflatable annulus or annular chamber which may be sealed in an inflated condition (filled with air or other gas) and placed around the periphery of the crystal, looking, in plan view, like the sheet 11 of FIG. 4(a). This annulus, made of thin flexible material transparent to X-rays provides a soft clamping member bearing upon the crystal edge. It may be pressed down upon the crystal by a mechanical clamp of annular form fixed to the mounting plate, or, it may be combined with a clamping arrangement as in FIG. 4, such that an annular flexible sheet 11 overlies the inflated annulus and forms a peripheral chamber outside it which is evacuated as in the arrangement of FIG. 4.

In a general refinement of the above apparatus, particularly for cases where the presence of a flaw in the crystal is accepted but where the flaw is required to be examined, the crystal mounting is oscillated through a small angle with a cyclic period shorter than but approximating to the exposure period so that, even if the flaw has distorted the relationship between the incident beam angle and the crystal lattice plane producing diffraction, at some point in the oscillation the relationship will be restored and a diffracted beam will be produced.

We claim:

1. X-ray diffraction apparatus comprising:
   (A) an X-ray source,
   (B) a crystal mounting plate transparent to X-rays,
   (C) means for imposing a curvature on the mounting plate of such form that, for a crystal slice clamped to the mounting plate the angle of incidence of X-rays diverging from said X-ray source to the crystal slice is substantially constant over the surface of the crystal slice, and
   (D) pneumatic pressure clamping means for clamping the crystal slice to the mounting plate, said clamping means including
      (i) a sheet of flexible material transparent to X-rays arranged to overlie the crystal slice and mounting plate so that a peripheral chamber is formed between the edge of the crystal slice and the sheet of material,
      (ii) said peripheral chamber being evacuated in operation,
      (iii) X-ray topographs of said crystal slice being thereby obtainable both by transmission and reflection.

2. X-ray diffraction apparatus according to claim 1, wherein said sheet of material has a hole arranged to expose the central part of the crystal slice.

3. X-ray diffraction apparatus according to claim 1 or claim 2, including a layer of elastic material transparent to X-rays covering the mounting plate to cushion the crystal slice against localized distortion that may arise from the presence of hard dust particles between the mounting plate and the crystal slice.

* * * * *